United States Patent
Isobe et al.

(10) Patent No.: US 11,248,207 B2
(45) Date of Patent: *Feb. 15, 2022

(54) METHOD FOR PRODUCING ALPHA-HYDROMUCONIC ACID

(71) Applicant: TORAY INDUSTRIES, INC., Tokyo (JP)

(72) Inventors: Kyohei Isobe, Kamakura (JP); Kenji Kawamura, Kamakura (JP); Masateru Ito, Kamakura (JP); Katsushige Yamada, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 24 days.

This patent is subject to a terminal disclaimer.

(21) Appl. No.: 16/304,803

(22) PCT Filed: May 30, 2017

(86) PCT No.: PCT/JP2017/020019
§ 371 (c)(1),
(2) Date: Nov. 27, 2018

(87) PCT Pub. No.: WO2017/209103
PCT Pub. Date: Dec. 7, 2017

(65) Prior Publication Data
US 2020/0232052 A1    Jul. 23, 2020

(30) Foreign Application Priority Data

May 31, 2016  (JP) .............................. JP2016-108640

(51) Int. Cl.
C12N 1/20    (2006.01)
C12P 7/44    (2006.01)
C12R 1/425   (2006.01)

(52) U.S. Cl.
CPC ............... *C12N 1/205* (2021.05); *C12N 1/20* (2013.01); *C12P 7/44* (2013.01); *C12R 2001/425* (2021.05)

(58) Field of Classification Search
None
See application file for complete search history.

(56) References Cited

U.S. PATENT DOCUMENTS

2009/0263874 A1* 10/2009 Moriya .................. C12R 1/425
435/110

OTHER PUBLICATIONS

Trias J et al. Induction of Yellow Pigmentation in Serratia marcescens. 1988. Applied and Environmental Microbiology. vol. 54, No. 12. p. 3138-3141. (Year: 1988).*
Extended European Search Report, dated Jan. 14, 2020, for European Application No. 17806657.7.
Johnson et al., "Enhancing muconic acid production from glucose and lignin-derived aromatic compounds via increased protocatechuate decarboxylase activity," Metabolic Engineering Communications, vol. 3, Apr. 22, 2016, XP055537227, pp. 111-119.
Tanaka et al., "*Desulfovirga adipica* gen. nov., sp. nov., an adipate-degrading, Gram-negative, sulfate-reducing bacterium," International Journal of Systematic and Evolutionary Microbiology, vol. 50, 2000, XP055523489, pp. 639-644.
Wu et al., "Microbial synthesis of cis,cis-muconic acid from benzoate by *Sphingobacterium* sp. mutants," Biochemical Engineering Journal, vol. 29, 2006, XP005335965. pp. 35-40.
Zhang et al., "Engineering *E. coli*—*E. coli* cocultures to production of muconic acid from glycerol," Microbial Cell Factories, vol. 14, 2015, XP002796637, pp. 1-10.

* cited by examiner

*Primary Examiner* — Paul J Holland
(74) *Attorney, Agent, or Firm* — Birch, Stewart, Kolasch & Birch, LLP

(57) ABSTRACT

Provided is a method of producing α-hydromuconic acid, the method including the step of culturing a microorganism belonging to the genus *Serratia* capable of producing α-hydromuconic acid.

9 Claims, No Drawings
Specification includes a Sequence Listing.

METHOD FOR PRODUCING ALPHA-HYDROMUCONIC ACID

TECHNICAL FIELD

The present invention relates to a method of producing α-hydromuconic acid using a microorganism belonging to the genus *Serratia*.

BACKGROUND ART

α-Hydromuconic acid (IUPAC name: (E)-hex-2-enedioic acid) is a dicarboxylic acid with six carbon atoms and a molecular weight of 144.13. α-Hydromuconic acid can be used as a raw material in polymerization with a polyhydric alcohol to produce a polyester or in polymerization with a polyamine to produce a polyamide. Moreover, a lactam produced by addition of ammonia to α-hydromuconic acid at its termini can be used even singly as a raw material for a polyamide.

In a report relating to the method of producing α-hydromuconic acid using a microorganism, α-hydromuconic acid (hex-2-enedioate) can be produced by an enzymatic reaction (a 3-hydroxyadipate dehydratase-mediated dehydration reaction) to dehydrate 3-hydroxyadipic acid (3-hydroxyadipate) as an intermediate in the pathway of adipic acid biosynthesis during the course of producing adipic acid from succinyl-CoA and acetyl-CoA as starting materials by a method using a non-naturally occurring microorganism (FIG. 3 in Patent Document 1).

Also, *Desulfovirga adipica* has been reported to produce α-hydromuconic acid in an amount to give a concentration of 0.86 mg/L within 17 days while degrading adipic acid for growth (Non-Patent Document 1).

Patent Document 2 describes methods of producing adipic acid, an adipic acid ester, or an adipic acid thioester using a biocatalyst or a microorganism and describes an α-hydromuconic acid (2,3-dehydroadipic acid) ester or an α-hydromuconic acid (2,3-dehydroadipic acid) thioester as an intermediate compound. It is described that the α-hydromuconic acid (2,3-dehydroadipic acid) ester or the α-hydromuconic acid (2,3-dehydroadipic acid) thioester is prepared by dehydration of a 3-hydroxyadipic acid ester or a 3-hydroxyadipic acid thioester.

PRIOR ART DOCUMENTS

Patent Documents

Patent Document 1: WO 2009/151728
Patent Document 2: WO 2009/113853

Non-Patent Document

Non-Patent Document 1: Int. J. Syst. Evol. Microbiol. 2000. March 50 Pt. 2: 639-44.

SUMMARY OF THE INVENTION

Problems to be Solved by the Invention

Patent Document 1 describes that 3-hydroxyadipic acid (3-hydroxyadipate) as an intermediate in the production of adipic acid can be dehydrated by an enzymatic reaction to produce α-hydromuconic acid (hex-2-enedioate) in an artificially modified microorganism that can produce adipic acid. However, no direct evidence for the dehydration reaction of 3-hydroxyadipic acid to α-hydromuconic acid by 3-hydroxyadipate dehydratase has been confirmed, and whether or not α-hydromuconic acid can be produced using a metabolic pathway of a microorganism has not been really examined. Furthermore, an enzyme called 3-hydroxyadipate dehydratase is not well known to those skilled in the art and, thus, α-hydromuconic acid has not been produced according to the description in Patent Document 1 from succinyl-CoA and acetyl-CoA as starting materials.

Non-Patent Document 1 reports that a naturally occurring microorganism produces α-hydromuconic acid but its productivity is extremely low, so that the method cannot be thought as a method of producing α-hydromuconic acid.

Patent Document 2 describes neither a method of producing α-hydromuconic acid (2,3-dehydroadipic acid) from an α-hydromuconic acid (2,3-dehydroadipic acid) ester or an α-hydromuconic acid (2,3-dehydroadipic acid) thioester, nor a method of producing α-hydromuconic acid (2,3-dehydroadipic acid) from 5-carboxy-2-pentenoyl-CoA (2,3-dehydroadipyl-CoA) as a specific example of the α-hydromuconic acid (2,3-dehydroadipic acid) thioester.

As seen above, no method has been actually available for the production of α-hydromuconic acid using a metabolic pathway of a microorganism. Thus, an object of the present invention is to provide a method of producing α-hydromuconic acid using a metabolic pathway of a microorganism.

Means for Solving the Problem

The inventors intensively studied to solve the above problems and consequently found that microorganisms belonging to the genus *Serratia* capable of using their metabolic pathway to produce α-hydromuconic acid exist in nature, and completed the following invention.

That is, the present invention provides the following items (1) to (7).

(1) A method of producing α-hydromuconic acid, the method comprising the step of culturing a microorganism belonging to the genus *Serratia* capable of producing α-hydromuconic acid.

(2) The method of producing α-hydromuconic acid according to (1), wherein the microorganism belonging to the genus *Serratia* has an enhanced enzymatic activity that catalyzes a reaction to produce 3-oxoadipyl-CoA and CoA from succinyl-CoA and acetyl-CoA.

(3) The method of producing α-hydromuconic acid according to (1) or (2), wherein the microorganism belonging to the genus *Serratia* is *Serratia grimesii*, *Serratia ficaria*, *Serratia fonticola*, *Serratia odorifera*, *Serratia plymuthica*, *Serratia entomophila*, or *Serratia nematodiphila*.

(4) The method of producing α-hydromuconic acid according to any of (1) to (3), wherein a medium for culturing the microorganism belonging to the genus *Serratia* contains at least one or more carbon sources selected from the group consisting of saccharides, succinic acid, 2-oxoglutaric acid, and glycerol.

(5) The method of producing α-hydromuconic acid according to any of (1) to (4), wherein the microorganism belonging to the genus *Serratia* is cultured in a medium that contains at least one or more inducers selected from the group consisting of ferulic acid, p-coumaric acid, benzoic acid, cis,cis-muconic acid, protocatechuic acid, and catechol.

(6) A microorganism belonging to the genus *Serratia* capable of producing α-hydromuconic acid, wherein an enzymatic activity that catalyzes a reaction to produce 3-oxoadipyl-CoA and CoA from succinyl-CoA and acetyl-CoA is enhanced in the microorganism belonging to the genus *Serratia*.

(7) The microorganism belonging to the genus *Serratia* according to (6), wherein the microorganism belonging to the genus *Serratia* is *Serratia grimesii*, *Serratia ficaria*, *Serratia fonticola*, *Serratia odorifera*, *Serratia plymuthica*, *Serratia entomophila*, or *Serratia nematodiphila*.

Effects of the Invention

By the present invention, α-hydromuconic acid can be obtained utilizing a metabolic pathway of a microorganism belonging to the genus *Serratia*.

MODE FOR CARRYING OUT THE INVENTION

The method of producing α-hydromuconic acid according to the present invention is characterized by comprising the step of culturing a microorganism belonging to the genus *Serratia* capable of producing α-hydromuconic acid. More particularly, the method is characterized by culturing a microorganism belonging to the genus *Serratia* capable of producing α-hydromuconic acid to utilize the metabolic pathway of the microorganism for the production of α-hydromuconic acid.

Specific examples of the microorganism belonging to the genus *Serratia* capable of producing α-hydromuconic acid include *Serratia grimesii*, *Serratia ficaria*, *Serratia fonticola*, *Serratia odorifera*, *Serratia plymuthica*, *Serratia entomophila*, and *Serratia nematodiphila*. The mechanism whereby the microorganism belonging to the genus *Serratia* can produce α-hydromuconic acid using its metabolic pathway remains unclear but the use of microorganisms belonging to the genus *Serratia* in a wastewater treatment method to reduce the amount of waste activated sludge (see JP 2002-18469 A) leads to a speculation that microorganisms belonging to the genus *Serratia* have a complex metabolic pathway different from those of microorganisms commonly used for the production of substances and produce α-hydromuconic acid through the metabolic pathway.

The above-listed microorganisms belonging to the genus *Serratia* are each known as naturally occurring microorganisms belonging to the genus *Serratia* and can be isolated from the natural environment, such as soils, or can also be purchased from institutions furnishing microorganisms, such as NBRC.

The microorganism belonging to the genus *Serratia* may be a strain of the microorganism in which a gene(s) is/are modified to increase the production of α-hydromuconic acid by genetic recombination or artificial mutagenesis according to a known procedure.

In the present invention, a preferably used microorganism belonging to the genus *Serratia* capable of producing α-hydromuconic acid is a microorganism belonging to the genus *Serratia* which can produce α-hydromuconic acid in an amount sufficient to give a concentration of not less than 1.0 mg/L in the culture supernatant within 48 hours when the microorganism belonging to the genus *Serratia* is cultured. More preferably, it is a microorganism belonging to the genus *Serratia* which can produce α-hydromuconic acid in an amount to give a concentration of not less than 1.0 mg/L in the culture supernatant when it is a wild-type strain and is not modified by genetic mutagenesis or genetic recombination.

Whether or not a microorganism belonging to the genus *Serratia* can produce α-hydromuconic acid in an amount to give a concentration of not less than 1.0 mg/L in the culture supernatant within 48 hours is evaluated by the following method. The amount of α-hydromuconic acid produced by a microorganism belonging to the genus *Serratia* and contained in the culture supernatant is measured by the following method.

A loopful of a subject microorganism belonging to the genus *Serratia* is inoculated in 5 mL of a preculture medium (culture medium composition: 10 g/L tryptone, 5 g/L yeast extract, 5 g/L sodium chloride) adjusted to pH 7 and cultured with shaking at 30° C. until the bacterial cells are well suspended. The resulting preculture is supplemented with 10 mL of 0.9% sodium chloride and then centrifuged to remove the supernatant from bacterial cells, and this operation is repeated three times in total to wash the bacterial cells. The washed bacterial cells are suspended in 1 mL of 0.9% sodium chloride and 0.5 mL of the suspension is inoculated in 5 mL of a main culture medium (culture medium composition: 10 g/L succinic acid, 10 g/L glucose, 1 g/L ammonium sulfate, 50 mM potassium phosphate, 0.025 g/L magnesium sulfate, 0.0625 mg/L iron sulfate, 2.7 mg/L manganese sulfate, 0.33 mg/L calcium chloride, 1.25 g/L sodium chloride, 2.5 g/L Bacto Tryptone, 1.25 g/L yeast extract) adjusted to pH 6.5 and cultured at 30° C. for 48 hours, and aliquots of the main culture are withdrawn over a time course of 48 hours.

Bacterial cells are separated by centrifugation of the main culture and the supernatant is analyzed by LC-MS/MS. The LC-MS/MS conditions for the analysis are as described below. For example, 1290 Infinity system (manufactured by Agilent Technologies, Inc.) can be used for HPLC and Triple-Quad LC/MS system (manufactured by Agilent Technologies, Inc.) can be used for MS/MS. Synergi hydro-RP column (manufactured by Phenomenex Inc.) can be used as the column.

HPLC Analysis Conditions

Column: 100 mm length×3 mm inner diameter with 2.5 μm particle size;
Mobile phase: 0.1% aqueous formic acid solution/methanol=70/30;
Flow rate: 0.3 mL/min;
Column temperature: 40° C.;
LC detector: DAD (210 nm).

MS/MS Analysis Condition

Ionization method: ESI in negative mode.

In the present invention, the microorganism belonging to the genus *Serratia* is cultured in a medium, preferably a liquid medium, containing a carbon source that ordinary microorganisms can metabolize. The term "metabolism" as used in the present invention refers to conversion of a chemical substance, which has been taken up from the extracellular environment or generated intracellularly from another chemical substance by a microorganism belonging to the genus *Serratia*, to another substance through an enzymatic reaction. The culture medium used in the present invention contains, in addition to the carbon source that the microorganism belonging to the genus *Serratia* can metabolize, appropriate amounts of a nitrogen source, inorganic salts, and, if necessary, organic trace nutrients such as amino acids and vitamins. Any of natural and synthetic culture media can be used as long as the medium contains the above-described nutrients.

Sugars can be preferably used as the carbon source that the microorganism belonging to the genus *Serratia* can metabolize. Specific examples of the sugars include monosaccharides such as glucose, sucrose, fructose, galactose, mannose, xylose, and arabinose, disaccharides and polysaccharides formed by linking these monosaccharides, and saccharified starch solution, molasses, and saccharified solution from cellulose-containing biomass each containing any of those saccharides.

Moreover, any carbon source other than the above-listed sugars can be preferably used as long as the carbon source is available for the growth of the microorganism belonging to the genus *Serratia*. Examples of such a carbon source include carboxylic acids such as acetic acid, succinic acid, lactic acid, fumaric acid, citric acid, propionic acid, malic acid, malonic acid, 2-oxoglutaric acid and pyruvic acid; monohydric alcohols such as methanol, ethanol and propanol; polyhydric alcohols such as glycerol, ethylene glycol and propanediol; hydrocarbons; fatty acids; and fats and oils; and preferred are succinic acid, 2-oxoglutaric acid and glycerol.

The above-listed carbon sources may be used individually or in combination. Specifically, among those carbon sources, one or more selected from the group consisting of sugars, succinic acid, 2-oxoglutaric acid, and glycerol may be metabolized to produce α-hydromuconic acid efficiently. The concentration of the carbon source in the culture medium is not limited to a particular concentration and can be appropriately selected depending on the type of the carbon source, and is preferably from 5 g/L to 300 g/L.

As a nitrogen source used for the culture of the microorganism belonging to the genus *Serratia*, for example, ammonia gas, aqueous ammonia, ammonium salts, urea, nitric acid salts, other supplementarily used organic nitrogen sources, such as oil cakes, soybean hydrolysate, casein degradation products, other amino acids, vitamins, corn steep liquor, yeast or yeast extract, meat extract, peptides such as peptone, and bacterial cells of various fermentative bacteria and hydrolysate thereof can be used. The concentration of the nitrogen source in the culture medium is not limited to a particular concentration and is preferably from 0.1 g/L to 50 g/L.

As inorganic salts used for the culture of the microorganism belonging to the genus *Serratia*, for example, phosphoric acid salts, magnesium salts, calcium salts, iron salts, and manganese salts can be appropriately added to the culture medium and used.

The culture conditions for the microorganism belonging to the genus *Serratia* to produce α-hydromuconic acid are established by appropriately adjusting or selecting, for example, the composition of the culture medium, culture temperature, stirring speed, pH, aeration rate, and inoculation amount depending on, for example, the type of the microorganism belonging to the genus *Serratia* to be used and external conditions. In cases where foam is formed in a liquid culture, an antifoaming agent such as a mineral oil, silicone oil, or surfactant may be appropriately added to the culture medium.

α-Hydromuconic acid can be produced by culturing the microorganism belonging to the genus *Serratia* used in the present invention in the above-described culture medium under the above-described culture conditions, and α-hydromuconic acid can be more efficiently produced by culturing the microorganism belonging to the genus *Serratia* under activation of a metabolic pathway required for the production of α-hydromuconic acid.

The method of activating the metabolic pathway is not limited to a particular method, and examples of the method include methods of increasing the expression level of an enzyme gene (or genes) in the metabolic pathway for the production of α-hydromuconic acid, methods of inducing the expression of the enzyme gene (or genes) by culturing the microorganism in a culture medium containing a substance to activate the metabolic pathway (hereinafter also referred to as inducer) for the production of α-hydromuconic acid, and methods of increasing the activity of the enzyme (or enzymes) encoded by the enzyme gene (or genes) through modification of the enzyme gene (or genes) by breeding techniques such as genetic recombination or genetic mutagenesis according to known procedures. These methods may be performed individually or in combination.

Examples of the method of increasing the expression level of the enzyme gene (or genes) include methods in which genetic engineering technology is applied to a microorganism belonging to the genus *Serratia* to increase the copy number(s) of the enzyme gene (or genes) in cells or to modify a functional region(s) in the vicinity of the coding region in the gene (in each of the genes); and the methods to increase the copy number(s) of the gene (genes) are preferable.

The inducer for use in the method to induce the expression of the enzyme gene (or genes) by culturing the microorganism belonging to the genus *Serratia* used in the present invention in a culture medium containing the inducer is not limited to a particular inducer as long as it is a substance that activates a metabolic pathway required for the production of α-hydromuconic acid, and, for example, aromatic compounds, aliphatic compounds having six or more carbon atoms, and other compounds having structures similar to those of the compounds, which are metabolized to 3-oxoadipyl-CoA as an intermediate and finally to compounds having a smaller number of carbon atoms, can be used. Examples of such compounds can be found, for example, using a database such as KEGG (Kyoto Encyclopedia of Genes and Genomes), and specific examples of the compounds include benzoic acid, cis,cis-muconic acid, terephthalic acid, protocatechuic acid, catechol, vanillin, coumaric acid, and ferulic acid. Preferred are ferulic acid, p-coumaric acid, and benzoic acid.

The above-described inducers may be used individually or in combination of two or more depending on the type of the microorganism belonging to the genus *Serratia* used for the production of α-hydromuconic acid. Moreover, any of the above-described inducers may be contained in a culture (preculture) medium for the growth of the microorganism belonging to the genus *Serratia* prior to the production of α-hydromuconic acid or contained in a culture medium used for the production of α-hydromuconic acid. The concentration of an inducer (the total concentration, when a plurality of inducers are contained) is not limited to a particular concentration when one or more inducers are contained in a culture medium, and the concentration is preferably from 1 mg/L to 10 g/L, more preferably 5 mg/L to 1 g/L.

Among those methods of increasing the activity of the enzyme (or enzymes) encoded by the enzyme gene (or genes) through modification of the enzyme gene (or genes) by breeding techniques such as genetic recombination or genetic mutagenesis according to known procedures, a preferred method is to introduce the enzyme gene (or genes) into a microorganism belonging to the genus *Serratia* used in the present invention by genetic recombination techniques.

Specific examples of the enzyme gene (or genes) include genes encoding enzymes that have the catalytic activity for the reaction to produce 3-oxoadipyl-CoA and CoA from succinyl-CoA and acetyl-CoA. In the present invention, by increasing the activity of an enzyme that has the catalytic activity for the reaction to produce 3-oxoadipyl-CoA and CoA from succinyl-CoA and acetyl-CoA in a microorganism belonging to the genus *Serratia* capable of producing α-hydromuconic acid, α-hydromuconic acid can be produced more efficiently.

The enzyme is not limited to a particular enzyme as long as it has the above-described activity. Specific examples of the enzymes that can be preferably used include acetyl-CoA acetyltransferase, β-ketoacyl-CoA acyltransferase, 3-oxoadipyl-CoA acyltransferase, β-ketoadipyl-CoA acyltransferase, acetyl-CoA C-acetyltransferase, acetoacetyl-CoA thiolase, beta-acetoacetyl coenzyme A thiolase, 2-methylacetoacetyl-CoA thiolase, 3-oxothiolase, acetyl coenzyme A thiolase, acetyl-CoA acetyltransferase, acetyl-CoA: N-acetyltransferase, acetyl-CoA C-acyltransferase, beta-ketothiolase, 3-ketoacyl-CoA thiolase, beta-ketoacyl coenzyme A thiolase, beta-ketoacyl-CoA thiolase, beta-ketoadipyl coenzyme A thiolase, beta-ketoadipyl-CoA thiolase, 3-ketoacyl coenzyme A thiolase, 3-ketoacyl thiolase, 3-ketothiolase, 3-oxoacyl-CoA thiolase, 3-oxoacyl-coenzyme A thiolase, 6-oxoacyl-CoA thiolase, acetoacetyl-CoA beta-ketothiolase, acetyl-CoA acyltransferase, ketoacyl-CoA acyltransferase, ketoacyl-coenzyme A thiolase, long-chain 3-oxoacyl-CoA thiolase, oxoacyl-coenzyme A thiolase, pro-3-ketoacyl-CoA thiolase, 3-oxoadipyl-CoA thiolase, and 3-oxo-5,6-didehydrosuberyl-CoA thiolase. The enzymes are not limited to enzymes classified as particular EC numbers and are preferably acyltransferases classified as EC2.3.1.-. Specific examples thereof include enzymes classified in EC2.3.1.174, EC2.3.1.9, EC2.3.1.16, and EC2.3.1.223.

Whether or not a protein encoded by a gene of unknown function is the above-described enzyme can be estimated by BLAST searching with the sequence of the gene on the web-site of, for example, NCBI (National Center for Biotechnology Information).

In cases where a gene encoding an enzyme that has the catalytic activity for the reaction to produce 3-oxoadipyl-CoA and CoA from succinyl-CoA and acetyl-CoA is introduced into a microorganism belonging to the genus *Serratia* by genetic recombination techniques to enhance the activity of an enzyme catalyzing the reaction to produce 3-oxoadipyl-CoA and CoA from succinyl-CoA and acetyl-CoA in a microorganism belonging to the genus *Serratia* used in the present invention, the origin of the gene encoding the enzyme is not limited to a particular organism, and genes that can be used are, for example, genes taken from naturally occurring microorganisms, artificially synthesized genes, and genes taken from microorganisms and optimized in terms of codon usage for expression in a microorganism belonging to the genus *Serratia* used in the present invention.

The microorganism from which a gene encoding an enzyme that catalyzes the reaction to produce 3-oxoadipyl-CoA and CoA from succinyl-CoA and acetyl-CoA is originated is not limited to a particular microorganism, and examples of the microorganism include: microorganisms belonging to the genus *Acinetobacter*, such as *Acinetobacter baylyi* and *Acinetobacter radioresistens*; microorganisms belonging to the genus *Aerobacter*, such as *Aerobacter cloacae*; microorganisms belonging to the genus *Alcaligenes*, such as *Alcaligenes faecalis*; microorganisms belonging to the genus *Bacillus*, such as *Bacillus badius*, *Bacillus magaterium*, and *Bacillus roseus*; microorganisms belonging to the genus *Brevibacterium*, such as *Brevibacterium iodinum*; microorganisms belonging to the genus *Corynebacterium*, such as *Corynebacterium acetoacidophilum*, *Corynebacterium acetoglutamicum*, *Corynebacterium ammoniagenes*, and *Corynebacterium glutamicum*; microorganisms belonging to the genus *Cupriavidus*, such as *Cupriavidus metallidurans*, *Cupriavidus necator*, *Cupriavidus numazuensis*, and *Cupriavidus oxalaticus*; microorganisms belonging to the genus *Delftia*, such as *Delftia acidovorans*; microorganisms belonging to the genus *Escherichia*, such as *Escherichia coli* and *Escherichia fergusonii*; microorganisms belonging to the genus *Hafnia*, such as *Hafnia alvei*; microorganisms belonging to the genus *Microbacterium*, such as *Microbacterium ammoniaphilum*; microorganisms belonging to the genus *Nocardioides*, such as *Nocardioides albus*; microorganisms belonging to the genus *Planomicrobium*, such as *Planomicrobium okeanokoites*; microorganisms belonging to the genus *Pseudomonas*, such as *Pseudomonas azotoformans*, *Pseudomonas chlororaphis*, *Pseudomonas fluorescens*, *Pseudomonas fragi*, *Pseudomonas putida*, *Pseudomonas reptilivora*, and *Pseudomonas taetrolens*; microorganisms belonging to the genus *Rhizobium*, such as *Rhizobium radiobacter*; microorganisms belonging to the genus *Rhodosporidium*, such as *Rhodosporidium toruloides*; microorganisms belonging to the genus *Saccharomyces*, such as *Saccharomyces cerevisiae*; microorganisms belonging to the genus *Serratia*, such as *Serratia entomophila*, *Serratia ficaria*, *Serratia fonticola*, *Serratia grimesii*, *Serratia nematodiphila*, *Serratia odorifera*, and *Serratia plymuthica*; microorganisms belonging to the genus *Shimwellia*, such as *Shimwellia blattae*; microorganisms belonging to the genus *Streptomyces*, such as *Streptomyces vinaceus*, *Streptomyces karnatakensis*, *Streptomyces olivaceus*, and *Streptomyces vinaceus*; microorganisms belonging to the genus *Yarrowia*, such as *Yarrowia lipolytica*; microorganisms belonging to the genus *Yersinia*, such as *Yersinia ruckeri*. The microorganism is preferably a microorganism belonging to the genus *Serratia* or the genus *Corynebacterium* and is further preferably *Serratia plymuthica* or *Corynebacterium glutamicum*.

In the present invention, the microorganism belonging to the genus *Serratia* in which the activity of an enzyme catalyzing the reaction to produce 3-oxoadipyl-CoA and CoA from succinyl-CoA and acetyl-CoA is enhanced refers to a microorganism belonging to the genus *Serratia* which has an enzyme that catalyzes the reaction to produce 3-oxoadipyl-CoA and CoA from succinyl-CoA and acetyl-CoA with an increased specific activity (Unit/mg) as compared to that of the control of the enzyme without any enhancement of activity. A microorganism belonging to the genus *Serratia* which has no genetic modification in the expression system of the enzyme that catalyzes the reaction to produce 3-oxoadipyl-CoA and CoA from succinyl-CoA and acetyl-CoA is used as a control.

The specific activity of an enzyme catalyzing the reaction to produce 3-oxoadipyl-CoA and CoA from succinyl-CoA and acetyl-CoA in a microorganism belonging to the genus *Serratia* is measured by culturing the microorganism belonging to the genus *Serratia* to prepare a cell-free extract (CFE) and using the resulting CFE as an enzyme solution. A method of preparing the enzyme solution is as follows.

A loopful of a subject microorganism belonging to the genus *Serratia* to be measured for the activity is inoculated in 5 mL of a preculture medium (culture medium composition: 10 g/L tryptone, 5 g/L yeast extract, 5 g/L sodium chloride) adjusted to pH 7 and cultured with shaking at 30° C. until the bacterial cells are well dispersed. The resulting preculture is supplemented with 10 mL of 0.9% sodium chloride and then centrifuged to remove the supernatant from bacterial cells, and this operation is repeated three times in total to wash the bacterial cells. The washed bacterial cells are suspended in 1 mL of 0.9% sodium chloride and 0.5 mL of the suspension is inoculated in 5 mL of a main culture medium (culture medium composition: 10 g/L succinic acid, 10 g/L glucose, 1 g/L ammonium sulfate, 50 mM potassium phosphate, 0.025 g/L magnesium sulfate, 0.0625 mg/L iron sulfate, 2.7 mg/L manganese sulfate, 0.33 mg/L calcium chloride, 1.25 g/L sodium chloride, 2.5 g/L Bacto Tryptone, 1.25 g/L yeast extract) adjusted to pH 6.5 and cultured with shaking at 30° C. for 3 hours.

Bacterial cells collected from 5 mL of the obtained main culture by centrifugation are suspended in 1 mL of a Tris-HCl buffer composed of 100 mM Tris-HCl (pH 8.0) and 1 mM dithiothreitol, and glass beads (with a diameter of 0.1 mm) are added to the resulting suspension to disrupt bacterial cells at 4° C. with an ultrasonic disruptor. The resulting bacterial homogenate is centrifuged and a cell-free extract (CFE) recovered as the supernatant is used as an enzyme solution.

The enzyme solution prepared by the above-described method is used to measure the rate of NADH consumption accompanied by 3-oxoadipyl-CoA reduction in the presence of an excess amount of a NADH-dependent 3-hydroxyacyl-CoA dehydrogenase in a reaction system, which dehydrogenase has a substrate specificity for 3-oxoadipyl-CoA produced by condensation between succinyl-CoA and acetyl-CoA, and the specific activity of the enzyme solution is calculated according to the Formula 1. In the Formula 1, the concentration of an enzyme solution (mg/ml) refers to the protein concentration of the enzyme solution.

Specific activity (Unit/mg)=[Δ340 nm×Total reaction volume (ml)]/[Concentration of an enzyme solution (mg/ml)×Volume of the enzyme solution (ml)×6.22×Optical path length (cm)]   (Formula 1)

The specific method to calculate the specific activity is as follows. The enzyme solution in a volume of 50 μL is mixed with 25 μL of the enzymatic reaction solution A (composition: 200 mM Tris-HCl (pH 8.0), 40 mM MgCl$_2$, 0.8 mM NADH, 2 mM DTT, 4.4 μg of 3-hydroxyacyl-CoA dehydrogenase (PaaH) derived from *Escherichia coli*) and the resulting mixture is incubated at 30° C. for 2 minutes. Subsequently, the total volume of the mixture of the above enzymatic reaction solution A and the above enzyme solution is added to a quartz cell filled with 25 μL of the enzymatic reaction solution B (composition: 2 mM acetyl-CoA, 0.4 mM succinyl-CoA) pre-incubated at 30° C., and the resulting mixture is quickly mixed to prepare a reaction solution. The decrease in absorbance at 340 nm is measured in the prepared reaction solution at 30° C. on a spectrophotometer and the obtained Δ340 value is applied to the Formula (1) to calculate the specific activity (Unit/mg). The protein concentration of the enzyme solution can be measured using, for example, the Quick Start Bradford protein assay (manufactured by Bio-Rad Laboratories, Inc.). For the spectrophotometer, the Ultrospec 3300 Pro (manufactured by GE Healthcare) can be used.

To produce α-hydromuconic acid more efficiently, for example, a method in which the function of an enzyme gene in the biosynthetic pathway for a by-product of α-hydromuconic acid, among the metabolic pathways of a microorganism belonging to the genus *Serratia* used in the present invention, is disrupted can be used, in addition to the above-described method.

After a recoverable amount of α-hydromuconic acid is produced in the culture of the microorganism belonging to the genus *Serratia*, the produced α-hydromuconic acid can be recovered. Recovery of the produced α-hydromuconic acid, such as isolation of the produced α-hydromuconic acid, can be performed according to a commonly used method in which the microorganism is stopped from growing once a product of interest is accumulated to an appropriate level, and the fermentation product is recovered from the culture. Specifically, α-hydromuconic acid can be isolated from the culture by, for example, column chromatography, ion exchange chromatography, activated charcoal treatment, crystallization, membrane separation, or distillation after separation of bacterial cells by, for example, centrifugation or filtration. More specifically, examples of the preferred recovery methods include methods in which water is removed from the culture by concentration using, for example, a reverse osmosis membrane or an evaporator to increase the concentration of α-hydromuconic acid and the crystals of α-hydromuconic acid and/or an α-hydromuconic acid salt are then produced by cooling or adiabatic crystallization and recovered by, for example, centrifugation or filtration; and methods in which an alcohol is added to the culture to produce an α-hydromuconic acid ester and the resulting α-hydromuconic acid ester is then recovered by distillation and then hydrolyzed to yield α-hydromuconic acid. However, the recovery method is not limited to the above-described methods.

EXAMPLES

The present invention will now be specifically described by way of Examples.

(Reference Example 1) Preparation of α-Hydromuconic Acid

An α-hydromuconic acid standard for use in analyses in Examples below was prepared by chemical synthesis. First, 1.5 L of super-dehydrated tetrahydrofuran (manufactured by Wako Pure Chemical Industries, Ltd.) was added to 13.2 g (0.1 mol) of succinic acid monomethyl ester (manufactured by Wako Pure Chemical Industries, Ltd.), and 16.2 g (0.1 mol) of carbonyldiimidazole (manufactured by Wako Pure Chemical Industries, Ltd.) was added thereto with stirring, followed by stirring the resulting mixture at room temperature for 1 hour under nitrogen atmosphere. To this suspension, 15.6 g (0.1 mol) of malonic acid monomethyl ester potassium salt and 9.5 g (0.1 mol) of magnesium chloride were added, and the resulting mixture was stirred at room temperature for 1 hour and then at 40° C. for 12 hours under nitrogen atmosphere. After completion of the reaction, 0.05 L of 1 mol/L hydrochloric acid was added to the reaction mixture, and the resulting mixture was extracted with ethyl acetate and purified by silica gel column chromatography (hexane:ethyl acetate=1:5) to yield 13.1 g of pure 3-oxohexanedicarboxylic acid dimethyl ester. Yield: 70%.

To 10 g (0.05 mol) of the obtained 3-oxohexanedicarboxylic acid dimethyl ester, 0.1 L of methanol (manufactured by Kokusan Chemical Co., Ltd.) was added, and 2.0 g (0.05 mol) of sodium borohydride (manufactured by Wako Pure Chemical Industries, Ltd.) was added thereto with stirring, and the resulting mixture was stirred at room temperature for 1 hour. Then, 0.02 L of 5 mol/L aqueous sodium hydroxide solution was added to the mixture, and the resulting mixture was stirred at room temperature for 2 hours. After completion of the reaction, the mixture was adjusted to pH 1 with 5 mol/L hydrochloric acid, concentrated with a rotary evaporator, and then recrystallized from water to yield 7.2 g of pure α-hydromuconic acid. Yield: 95%.

¹H-NMR Spectrum of α-Hydromuconic Acid

¹H-NMR (400 MHz, CD3OD): δ2.48 (m, 4H), δ5.84 (d, 1H), δ6.96 (m, 1H).

(Example 1) α-Hydromuconic Acid Production Test

The microorganisms belonging to the genus *Serratia* shown in Table 1 (all of them were purchased from institutions furnishing microorganisms, which are indicated in the strain names) were investigated for their ability to produce α-hydromuconic acid. In 5 mL of a culture medium containing 10 g/L tryptone, 5 g/L yeast extract, and 5 g/L sodium chloride and adjusted to pH 7, a loopful of each microorganism belonging to the genus *Serratia* was inoculated and cultured with shaking at 30° C. until the bacterial cells were well suspended (preculture). The resulting culture was supplemented with 10 mL of 0.9% sodium chloride and the bacterial cells were then separated by centrifugation to remove the supernatant for washing the bacterial cells, and this operation was repeated three times in total, followed by suspending the bacterial cells in 1 mL of 0.9% sodium chloride. The suspension in a volume of 0.5 mL was added to 5 mL of a culture medium with the composition indicated below and incubated with shaking at 30° C. for 48 hours:
Succinic acid, 10 g/L;
Glucose, 10 g/L;
Ammonium sulfate, 1 g/L;
Potassium phosphate, 50 mM;
Magnesium sulfate, 0.025 g/L;
Iron sulfate, 0.0625 mg/L;
Manganese sulfate, 2.7 mg/L;
Calcium chloride, 0.33 mg/L;
Sodium chloride, 1.25 g/L;
Bacto Tryptone, 2.5 g/L;
Yeast extract, 1.25 g/L;
pH 6.5.

Quantitative Analysis of α-Hydromuconic Acid

The main culture was centrifuged to separate the supernatant from bacterial cells and the resulting supernatant was analyzed by LC-MS/MS. Quantitative analysis of α-hydromuconic acid was carried out by LC-MS/MS under the following conditions:
HPLC: 1290 Infinity (manufactured by Agilent Technologies, Inc.);
Column: Synergi hydro-RP (manufactured by Phenomenex Inc.), 100 mm length×3 mm inner diameter with 2.5 μm particle size;
Mobile phase: 0.1% aqueous formic acid solution/methanol=70/30;
Flow rate: 0.3 mL/min;
Column temperature: 40° C.;
LC detector: DAD (210 nm);
MS/MS: Triple-Quad LC/MS (manufactured by Agilent Technologies, Inc.);
Ionization method: ESI in negative mode.

The results of quantitative analysis of α-hydromuconic acid accumulated in the respective culture supernatants are shown in Table 1. These results confirmed that any of the microorganisms belonging to the genus *Serratia* had the ability to produce α-hydromuconic acid.

TABLE 1

| Test microorganism | Production of α-hydromuconic acid (mg/L) |
|---|---|
| *Serratia grimesii* NBRC13537 | 3.1 |
| *Serratia ficaria* NBRC102596 | 6.0 |
| *Serratia plymuthica* NBRC102599 | 3.0 |
| *Serratia fonticola* NBRC102597 | 4.3 |
| *Serratia odorifera* NBRC102598 | 2.8 |
| *Serratia entomophila* DSM12358 | 1.2 |
| *Serratia nemalodiphila* DSM21420 | 1.1 |

(Example 2) α-Hydromuconic Acid Production Test Using Inducers

The preculture and the main culture under the same conditions as in Example 1 were performed on the microorganisms belonging to the genus *Serratia* shown in Table 2 to analyze quantitatively α-hydromuconic acid in the culture supernatant, except that ferulic acid, p-coumaric acid, benzoic acid, cis,cis-muconic acid, protocatechuic acid, and catechol were added as inducers to the preculture medium to a final concentration of 2.5 mM each. The respective results are shown in Table 2. These results indicate that the addition of the inducers to the preculture medium increased the production of α-hydromuconic acid.

TABLE 2

| | Production of α-hydromuconic acid (mg/L) | |
|---|---|---|
| Test microorganism | without addition of inducers | with addition of inducers |
| *Serratia grimesii* NBRC13537 | 3.1 | 8.1 |
| *Serratia ficaria* NBRC102596 | 6.0 | 11.8 |
| *Serratia plymuthica* NBRC102599 | 3.0 | 5.1 |
| *Serratia fonticola* NBRC102597 | 4.3 | 8.6 |
| *Serratia odorifera* NBRC102598 | 2.8 | 5.9 |
| *Serratia entomophila* DSM12358 | 1.2 | 1.9 |
| *Serratia nematodiphila* DSM21420 | 1.1 | 2.1 |

(Example 3) α-Hydromuconic Acid Production Test Using Two Kinds of Carbon Sources The microorganisms belonging to the genus *Serratia* shown in Table 3 were precultured using the same culture medium as in Example 2 and then cultured in each culture medium containing compounds shown in Table 3 as carbon sources at a concentration of 10 g/L each under the same conditions as in Example 2 to analyze quantitatively α-hydromuconic acid in the culture supernatant. The respective results are shown in Table 3. These results indicate that the microorganisms were able to produce α-hydromuconic acid efficiently even in cases where they were cultured using carbon sources other than glucose and succinic acid.

TABLE 3

Production of α-hydromuconic acid (mg/L)
(with addition of inducers)
Carbon sources

| Test microorganism | glucose glycerol | glycerol succinic acid | xylose succinic acid | arabinose succinic acid | glucose 2-oxoglutaric acid | glycerol 2-oxoglutaric acid | xylose 2-oxoglutaric acid | arabinose 2-oxoglutaric acid |
|---|---|---|---|---|---|---|---|---|
| S. grimesii NBRC13537 | 3.1 | 13.7 | 11.3 | 4.6 | 4.5 | 6.3 | 3.9 | 4.2 |
| S. ficaria NBRC102596 | 3.0 | 16.6 | 9.7 | 4.4 | 2.2 | 9.4 | 2.6 | 3.1 |
| S. plymuthica NBRC102599 | 2.3 | 2.9 | 4.0 | 3.3 | 1.8 | 1.9 | 1.7 | 1.4 |

(Example 4) α-Hydromuconic Acid Production Test Using Two Kinds of Carbon Sources at Different Concentrations The microorganisms belonging to the genus *Serratia* shown in Table 4 were precultured using the same culture medium as in Example 2 and then cultured in each culture medium containing compounds shown in Table 4 as carbon sources at the indicated concentrations for 48 to 120 hours under the same conditions as in Example 2 to analyze quantitatively α-hydromuconic acid in the culture supernatant. The respective results are shown in Table 4. These results indicate that the microorganisms were able to produce α-hydromuconic acid even in cases where the ratio of carbon sources added to the culture medium was changed.

TABLE 4

Production of α-hydromuconic acid (mg/L)
(with addition of inducers)
Carbon sources

| Test microorganism | 25 g/L glucose 10 g/L succinic acid | 50 g/L glucose 10 g/L succinic acid | 25 g/L xylose 10 g/L succinic acid | 50 g/L xylose 10 g/L succinic acid | 10 g/L glucose 20 g/L succinic acid | 100 g/L glucose 20 g/L succinic acid | 50 g/L xylose 20 g/L succinic acid |
|---|---|---|---|---|---|---|---|
| S. grimesii NBRC13537 | 10.9 | 16.1 | 9.1 | 14.5 | 15.8 | 52.6 | 100.7 |
| S. ficaria NBRC102596 | 12.0 | 17.2 | 36.2 | 56.1 | 10.8 | 39.9 | 47.9 |
| S. plymuthica NBRC102599 | 4.0 | 5.2 | 4.8 | 5.4 | 6.0 | 7.8 | 7.0 |

(Example 5) α-Hydromuconic Acid Production Test Using a Single Carbon Source

The microorganisms belonging to the genus *Serratia* shown in Table 5 were precultured using the same culture medium as in Example 1 and then cultured in each culture medium containing any one of succinic acid, glucose, and glycerol as a carbon source at a concentration of 10 g/L under the same conditions as in Example 1 to analyze quantitatively α-hydromuconic acid in the culture supernatant. The respective results are shown in Table 5. Furthermore, the same experiment was repeated except that the preculture media were modified similarly to Example 2, and the productions of α-hydromuconic acid resulting from the further addition of the inducers to the preculture media are shown in Table 6. These results indicate that the microorganisms were able to produce α-hydromuconic acid even in cases where a single carbon source was used, and also indicate that the production of α-hydromuconic acid was increased by adding the inducers to the preculture medium even in cases where a single carbon source was used.

TABLE 5

Production of α-hydromuconic acid (mg/L)
(without addition of inducers)
Carbon source

| Test microorganism | succinic acid | glucose | glycerol | xylose | arabinose | 2-oxoglutaric acid |
|---|---|---|---|---|---|---|
| S. grimesii NBRC13537 | 1.0 | 2.2 | 1.8 | 2.8 | 1.9 | 1.0 |
| S. ficaria NBRC102596 | 1.2 | 3.3 | 4.0 | 2.9 | 2.2 | 1.1 |
| S. plymuthica NBRC102599 | 1.0 | 1.3 | 1.3 | 1.3 | 1.4 | 1.6 |

TABLE 6

Production of α-hydromuconic acid (mg/L)
(with addition of inducers)
Carbon source

| Test microorganism | succinic acid | glucose | glycerol | xylose | arabinose | 2-oxoglutaric acid |
|---|---|---|---|---|---|---|
| S. grimesii NBRC13537 | 2.0 | 3.1 | 3.8 | 5.3 | 3.8 | 1.8 |
| S. ficaria NBRC102596 | 1.7 | 4.2 | 5.9 | 5.1 | 4.4 | 1.3 |
| S. plymuthica NBRC102599 | 1.6 | 1.6 | 1.7 | 2.0 | 2.0 | 1.9 |

(Example 6) α-Hydromuconic Acid Production Test Using Ferulic Acid as an Inducer at Different Concentrations The microorganisms belonging to the genus *Serratia* shown in Table 7 were precultured in the same preculture medium as in Example 1, except that ferulic acid was selected from the substances added as inducers to the preculture medium in Examples 2 to 5, and added to the respective concentrations shown in Table 7. The preculture and the main culture were performed under the same conditions as in Example 1 except for the preculture medium to analyze quantitatively α-hydromuconic acid in the culture supernatant. The respective results are shown in Table 7. These results indicate that the production of α-hydromuconic acid was increased even in cases where only ferulic acid was added as an inducer to the preculture medium.

TABLE 7

| Test microorganism | Production of α-hydromuconic acid (mg/L) Concentration of added ferulic acid (mM) | | | | | | |
|---|---|---|---|---|---|---|---|
| | 0.00 | 0.05 | 0.10 | 0.25 | 0.50 | 1.00 | 2.50 |
| S. grimesii NBRC13537 | 3.1 | 3.8 | 4.2 | 4.7 | 4.7 | 4.7 | 5.1 |
| S. ficaria NBRC102596 | 6.0 | 6.7 | 7.3 | 8.2 | 8.3 | 8.7 | 9.3 |
| S. plymuthica NBRC102599 | 3.0 | 3.4 | 3.7 | 4.0 | 4.7 | 5.0 | 5.1 |

(Example 7) α-Hydromuconic Acid Production Test Using p-Coumaric Acid as an Inducer at Different Concentrations The microorganism belonging to the genus *Serratia* shown in Table 8 was precultured in the same preculture medium as in Example 1, except that p-coumaric acid was selected from the substances added as inducers to the preculture medium in Examples 2 to 5, and was added to the respective concentrations shown in Table 8. The preculture and the main culture were performed under the same conditions as in Example 1 except for the preculture medium to analyze quantitatively α-hydromuconic acid in the culture supernatant. The respective results are shown in Table 8. These results indicate that the production of α-hydromuconic acid was increased even in cases where only p-coumaric acid was added as an inducer to the preculture medium.

TABLE 8

| Test microorganism | Production of α-hydromuconic acid (mg/L) Concentration of added p-coumaric acid (mM) | | | | | | |
|---|---|---|---|---|---|---|---|
| | 0.00 | 0.05 | 0.10 | 0.25 | 0.50 | 1.00 | 2.50 |
| S. grimesii NBRC13537 | 3.1 | 4.0 | 4.2 | 4.4 | 4.8 | 5.5 | 6.3 |

(Example 8) α-Hydromuconic Acid Production Test Using Benzoic Acid as an Inducer The microorganisms belonging to the genus *Serratia* shown in Table 9 were precultured in the same preculture medium as in Example 1, except that benzoic acid was selected from the substances added as inducers to the preculture medium in Examples 2 to 5, and was added to a concentration of 2.5 mM. The preculture and the main culture were performed under the same conditions as in Example 1 except for the preculture medium to analyze quantitatively α-hydromuconic acid in the culture supernatant. The respective results are shown in Table 9. These results indicate that the production of α-hydromuconic acid was increased even in cases where only benzoic acid was added as an inducer to the preculture medium.

TABLE 9

| | Production of α-hydromuconic acid (mg/L) | |
|---|---|---|
| Test microorganism | without addition of inducers | with addition of benzoic acid at 2.5 mM |
| S. grimesii NBRC13537 | 3.1 | 4.2 |
| S. plymuthica NBRC102599 | 3.0 | 3.5 |

(Example 9) Production Example of α-Hydromuconic Acid

A loopful of S. grimesii NBRC13537, which was identified in Example 1 as a microorganism belonging to the genus Serratia capable of producing α-hydromuconic acid, was inoculated in 5 mL of LB medium and cultured with shaking at 30° C. until the bacterial cells were well suspended. The culture in a volume of 2 mL was added to 100 mL of a culture medium containing 10 g/L tryptone, 5 g/L yeast extract, 5 g/L sodium chloride, and 0.5 mM ferulic acid and cultured with shaking at 30° C. until the bacterial cells were well suspended (preculture). The preculture was washed three times similarly to Example 1 with 200 mL of 0.9% sodium chloride and the resulting bacterial cells were then suspended in 10 mL of 0.9% sodium chloride. The suspension in a volume of 10 mL was added to 100 mL of the culture medium described in Example 1 and containing 100 g/L glucose and 20 g/L succinic acid as carbon sources, and the microorganism was cultured with shaking at 30° C. for 120 hours. The supernatant separated from bacterial cells by centrifugation of the culture was analyzed similarly to Example 1 by LC-MS/MS. As a result, the concentration of α-hydromuconic acid accumulated in the culture supernatant was 46 mg/L.

Next, the culture supernatant was concentrated under reduced pressure to obtain 11 mL of a concentrated α-hydromuconic acid solution at a concentration of 420 mg/L. This concentrated solution was injected into an HPLC system connected to a fraction collector, and fractions with the same retention time as the α-hydromuconic acid standard were collected. This operation was repeated 10 times to obtain an aqueous solution of α-hydromuconic acid free from impurities present in the culture. The preparative HPLC used for the preparation of α-hydromuconic acid was performed under the following conditions:
HPLC: Shimadzu 20A (manufactured by Shimadzu Corporation);
Column: Synergi hydro-RP (manufactured by Phenomenex Inc.), 250 mm length×10 mm inner diameter with 4 µm particle size;
Mobile phase: 5 mM aqueous formic acid solution/acetonitrile=98/2;
Flow rate: 4 mL/min;
Injection volume: 1 mL;
Column temperature: 45° C.;
Detector: UV-VIS (210 nm);
Fraction collector: FC204 (manufactured by Gilson Inc.).

Subsequently, the aqueous α-hydromuconic acid solution was concentrated under reduced pressure to yield 3.8 mg of crystals. The analysis of the crystals by $^1$H-NMR confirmed that the obtained crystals were α-hydromuconic acid.

(Reference Example 2) Culture without Addition of Any Carbon Source

The microorganisms belonging to the genus Serratia shown in Table 2 were cultured under the same conditions as in Example 1 except for using a culture medium without glucose and succinic acid in its composition to analyze quantitatively α-hydromuconic acid. As a result, α-hydromuconic acid was not detected in the culture supernatant. These results indicate that the α-hydromuconic acid produced by each of the microorganisms belonging to the genus Serratia in Examples 1 to 8 was obtained from the metabolism of glucose, succinic acid, arabinose, 2-oxoglutaric acid, xylose, or glycerol as a carbon source.

(Reference Example 3) Microorganisms Incapable of Producing α-Hydromuconic Acid

For the purpose of examining the ability of the microorganisms shown in Table 10 to produce α-hydromuconic acid, those microorganisms were cultured under the same conditions as in Example 1 to analyze quantitatively α-hydromuconic acid. All results were below detection limit and α-hydromuconic acid was not detected in the culture supernatant. Here, the detection limit is 0.1 mg/L.

TABLE 10

| Test microorganism | α-hydromuconic acid (mg/L) |
|---|---|
| Zymomonas mobilis NBRC13756 | N.D. |
| Microbacterium ammoniaphilum ATCC15354 | N.D. |
| Planomicrobium okeanokoites NBRC12536 | N.D. |
| Yersinia ruckeri NBRC102019 | N.D. |

(Example 10) Construction of a Plasmid for the Expression of a S. Plymuthica-Derived Gene Encoding an Enzyme that Catalyzes the Reaction to Produce 3-Oxoadipyl-CoA and CoA from Succinyl-CoA and Acetyl-CoA From the result of BLAST searching, the sequence of a gene from S. plymuthica NBRC102599, which is represented by SEQ ID NO: 4, was estimated to encode an enzyme which is 3-oxoadipyl CoA thiolase (PcaF) that catalyzes the reaction to produce 3-oxoadipyl-CoA and CoA from succinyl-CoA and acetyl-CoA. For the expression of the above gene, the plasmid pBBR1MCS-2::SppcaF was constructed. The pBBR1MCS-2 vector, which is able to self-replicate in the genus Serratia (M E Kovach, (1995), Gene 166: 175-176), was cleaved with XhoI to obtain pBBR1MCS-2/XhoI. Primers (SEQ ID NOs: 2 and 3) were designed to amplify a 200-bp region (SEQ ID NO: 1) upstream of the ORF of the gapA gene by PCR using the genome of Escherichia coli K-12 MG1655 as a template, and PCR was performed conventionally. The resulting fragment and pBBR1MCS-2/XhoI were ligated together using the In-Fusion HD Cloning Kit (manufactured by Clontech Laboratories) and the resulting plasmid that was confirmed by a conventional method to have the corresponding base sequence was designated as pBBR1MCS-2::PgapA. Then, pBBR1MCS-2::PgapA was cleaved with ScaI to obtain pBBR1MCS-2::PgapA/ScaI. Primers (SEQ ID NOs: 5 and 6) were designed to amplify the ORF (SEQ ID NO: 4) of the gene encoding the enzyme that catalyzes the reaction to produce 3-oxoadipyl-CoA and CoA from succinyl-CoA and acetyl-CoA by PCR using the genome of *S. plymuthica* NBRC102599 as a template, and PCR was performed conventionally. The resulting fragment and pBBR1MCS-2::PgapA/ScaI were ligated together using the In-Fusion HD Cloning Kit and the resulting plasmid that was confirmed by a conventional method to have the corresponding base sequence was designated as pBBR1MCS-2::SppcaF.

(Example 11) Construction of a Plasmid for the Expression of a *C. Glutamicum*-Derived Gene Encoding an Enzyme that Catalyzes the Reaction to Produce 3-Oxoadipyl-CoA and CoA from Succinyl-CoA and Acetyl-CoA For the purpose of inducing the expression of an enzyme from *Corynebacterium glutamicum* ATCC13032 that catalyzes the reaction to produce 3-oxoadipyl-CoA and CoA from succinyl-CoA and acetyl-CoA, primers (SEQ ID NOs: 7 and 8) were designed to amplify the ORF of an acetyl-CoA acetyltransferase gene (pcaF) (GenBank accession No. NC_003450; GI No. 19553591) by PCR using the genome of *Corynebacterium glutamicum* ATCC13032 as a template, and PCR was performed conventionally. The resulting fragment and pBBR1MCS-2::PgapA/ScaI were ligated together using the In-Fusion HD Cloning Kit and the resulting plasmid that was confirmed by a conventional method to have the corresponding base sequence was designated as pBBR1MCS-2::CgpcaF.

(Example 12) Introduction of Plasmids into Microorganisms Belonging to the Genus *Serratia*

The plasmids constructed in Examples 10 and 11, pBBR1MCS-2::SppcaF and pBBR1MCS-2::CgpcaF, and the pBBR1MCS-2 vector as a control were each introduced into the microorganisms belonging to the genus *Serratia* shown in Table 11 by electroporation (N M Calvin, P C Hanawalt. J. Bacteriol., 170 (1988), pp. 2796-2801). The transformed microorganisms belonging to the genus *Serratia* were incubated on LB agar plates containing 25 µg/mL kanamycin at 30° C. and grown for 1 to 2 days.

(Example 13) Measurement of the Activity of an Enzyme that Catalyzes the Reaction to Produce 3-Oxoadipyl-CoA and CoA from Succinyl-CoA and Acetyl-CoA The transformed microorganisms belonging to the genus *Serratia* obtained in Example 12 were used to compare the specific activities of the enzymes catalyzing the reaction to produce 3-oxoadipyl-CoA and CoA from succinyl-CoA and acetyl-CoA.

(a) Overexpression and Purification of PaaH from *E. Coli*

PaaH for use in the measurement of the activity of an enzyme catalyzing the reaction to produce 3-oxoadipyl-CoA and CoA from succinyl-CoA and acetyl-CoA was overexpressed and purified. First, pCDF-1b was cleaved with BamHI to obtain pCDF-1b/BamHI. Primers (SEQ ID NOs: 9 and 10) were designed to amplify the paaH gene (GenBank accession No. NC_000913; GI No. 945940) by PCR using the genome of *Escherichia coli* K-12 MG1655 as a template, and PCR was performed conventionally. The resulting fragment and pCDF-1b/BamHI were ligated together using the In-Fusion HD Cloning Kit and the resulting plasmid that was continued by a conventional method to have the corresponding base sequence was designated as pCDF-1b:EcpaaH. Then, pCDF-1b:EcpaaH was introduced into *Escherichia coli* BL21 (DE3) and the resulting transformant was cultured aerobically in LB medium containing 50 µg/mL streptomycin (37° C.), to which isopropylthiogalactoside was added to a final concentration of 1 mM when the OD600 reached around 0.3, to induce the expression of paaH (aerobically, 37° C., overnight). Centrifuged bacterial cells were suspended in 20 mM Tris-HCl (pH 8.0) and disrupted on ice with an ultrasonic homogenizer and then centrifuged to recover the supernatant as a cell-free extract. The obtained cell-free extract was purified with the His-Bind resin (manufactured by Merck) and then centrifuged in Amicon Ultra 3K (manufactured by Merck) to obtain a concentrated solution, which was then diluted with 20 mM Tris-HCl (pH 8.0) to obtain a PaaH enzyme solution (0.31 mg/mL). The concentration of the enzyme was determined using the Quick Start Bradford protein assay (manufactured by Bio-Rad Laboratories, Inc.).

(b) Preparation of an Enzyme Solution

One loopful of the microorganisms belonging to the genus *Serratia* shown in Table 11 to which the plasmid pBBR1MCS-2 was introduced, as the microorganisms in which the activity of an enzyme catalyzing the reaction to produce 3-oxoadipyl-CoA and CoA from succinyl-CoA and acetyl-CoA was not enhanced, and one loopful of the microorganisms belonging to the genus *Serratia* shown in Table 11 to which the plasmid pBBR1MCS-2::CgpcaF was introduced, as the microorganisms in which the activity of an enzyme catalyzing the reaction to produce 3-oxoadipyl-CoA and CoA from succinyl-CoA and acetyl-CoA was enhanced, were respectively inoculated in 5 mL of a preculture medium with the composition indicated below and cultured with shaking at 30° C. until the bacterial cells were well suspended. The culture was supplemented with 10 mL of 0.9% sodium chloride and the bacterial cells were then separated by centrifugation to remove the supernatant for washing the bacterial cells, and this operation was repeated three times in total, followed by suspending the bacterial cells in 1 mL of 0.9% sodium chloride. The suspension in a volume of 0.5 mL was added to 5 mL of a main culture medium with the composition indicated below and incubated with shaking at 30° C. for 3 hours.

The above culture in a volume of 5 mL was centrifuged to collect bacterial cells and the resulting bacterial cells were suspended in 1 mL of a Tris-HCl buffer described below. Glass beads (with a diameter of 0.1 mm) were added to the above bacterial cell suspension to disrupt the bacterial cells at 4° C. with the Micro Smash (manufactured by TOMY Seiko Co., Ltd.). After disrupting bacterial cells as described above, a cell-free extract (CFE) obtained as the supernatant by centrifugation was used as an enzyme solution in the following experiments.

(c) Measurement of the Activity of an Enzyme that Catalyzes the Reaction to Produce 3-Oxoadipyl-CoA and CoA from Succinyl-CoA and Acetyl-CoA The concentration of proteins in the CFE obtained in (b) was measured with the Quick Start Bradford protein assay (manufactured by Bio-Rad Laboratories, Inc.). Next, 25 µL of the enzymatic reaction solution A with the composition indicated below and 50 µL of the CFE were mixed and incubated (at 30° C. for 2 min). Subsequently, the total volume of the above-described solution containing the enzymatic reaction solution A and the CFE was added to a quartz cell filled with 25 µL of the enzymatic reaction solution B pre-incubated at 30° C., and the resulting mixture was quickly mixed to start the measurement of the activity (at 30° C.). The decrease in absorbance at 340 nm was measured with a spectrophotometer (Ultrospec 3300 Pro manufactured by GE Healthcare) and the obtained Δ340 value was applied to the Formula (1) to calculate the specific activity of each enzyme solution. The respective results of the calculation are shown in Table 11.

These results indicate that the specific activity of the enzyme catalyzing the reaction to produce 3-oxoadipyl-CoA and CoA from succinyl-CoA and acetyl-CoA was increased in the microorganism strains belonging to the genus *Serratia* into which the corresponding enzyme had been introduced, as compared to the unintroduced strains.

Pre-Culture Medium

Tryptone, 10 g/L;
Yeast extract, 5 g/L;
Sodium chloride, 5 g/L;
pH 7.

Main Culture Medium

Succinic acid, 10 g/L;
Glucose, 10 g/L;
Ammonium sulfate, 1 g/L;
Potassium phosphate, 50 mM;
Magnesium sulfate, 0.025 g/L;
Iron sulfate, 0.0625 mg/L;
Manganese sulfate, 2.7 mg/L;
Calcium chloride, 0.33 mg/L;
Sodium chloride, 1.25 g/L;
Bacto Tryptone, 2.5 g/L;
Yeast extract, 1.25 g/L;
pH 6.5.

Tris-HCl Buffer

Tris-HCl (pH 8.0), 100 mM;
Dithiothreitol, 1 mM.

Enzymatic Reaction Solution A

Tris-HCl (pH 8.0), 200 mM;
MgCl$_2$, 40 mM;
NADH, 0.8 mM;
DTT, 2 mM;
PaaH, 4.4 µg.

Enzymatic Reaction Solution B

Acetyl-CoA, 2 mM;
Succinyl-CoA, 0.4 mM.

TABLE 11

| | Specific activity (Unit/mg) | |
|---|---|---|
| Test microorganism | pBBR1MCS-2 | pBBR1MCS-2::CgpcaF |
| *Serratia grimesii* NBRC13537 | 0.0059 | 0.019 |
| *Serratia ficaria* NBRC102596 | 0.0082 | 0.017 |

TABLE 11-continued

| | Specific activity (Unit/mg) | |
|---|---|---|
| Test microorganism | pBBR1MCS-2 | pBBR1MCS-2::CgpcaF |
| *Serratia fonticola* NBRC102597 | 0.0049 | 0.015 |
| *Serratia odorifera* NBRC102598 | 0.0043 | 0.0072 |
| *Serratia plymuthica* NBRC102599 | 0.013 | 0.018 |
| *Serratia entomophila* DSM12358 | 0.0070 | 0.016 |
| *Serratia nematodiphila* DSM21420 | 0.0092 | 0.015 |

(Example 14) α-Hydromuconic Acid Production Test Using Microorganisms Belonging to the Genus *Serratia* in which an Enzyme that Catalyzes the Reaction to Produce 3-Oxoadipyl-CoA and CoA from Succinyl-CoA and Acetyl-CoA is Expressed by Genetic Recombination The microorganisms belonging to the genus *Serratia* shown in Table 12 and the microorganisms belonging to the genus *Serratia* generated in Example 12 into which an enzyme catalyzing the reaction to produce 3-oxoadipyl-CoA and CoA from succinyl-CoA and acetyl-CoA had been introduced by genetic recombination were investigated for their ability to produce α-hydromuconic acid. A loopful of each microorganism belonging to the genus *Serratia* was inoculated in 5 mL of a culture medium containing 10 g/L tryptone, 5 g/L yeast extract, 5 g/L sodium chloride, and 25 µm/mL kanamycin and adjusted to pH 7 and then cultured with shaking at 30° C. until the bacterial cells were well suspended (preculture). The culture in a volume of 0.25 mL was added to 5 mL of a culture medium with the composition indicated below and incubated with shaking at 30° C. for 24 hours in the main culture:

Succinic acid, 10 g/L;
Glucose, 10 g/L;
Ammonium sulfate, 1 g/L;
Potassium phosphate, 50 mM;
Magnesium sulfate, 0.025 g/L;
Iron sulfate, 0.0625 mg/L;
Manganese sulfate, 2.7 mg/L;
Calcium chloride, 0.33 mg/L;
Sodium chloride, 1.25 g/L;
Bacto Tryptone, 2.5 g/L;
Yeast extract, 1.25 g/L;
Kanamycin, 25 mL;
pH 6.5.

The supernatant separated from bacterial cells by centrifugation of the main culture was analyzed similarly to Example 1 by LC-MS/MS. The results of quantitative analysis of α-hydromuconic acid accumulated in the respective culture supernatants are shown in Table 12.

These results indicate that the concentration of the accumulated α-hydromuconic acid was increased in the strains into which an enzyme catalyzing the reaction to produce 3-oxoadipyl-CoA and CoA from succinyl-CoA and acetyl-CoA had been introduced, as compared to the unintroduced strains. Thus, the results from this Example and Example 12 indicate that enhancement of the enzymatic activity catalyzing the reaction to produce 3-oxoadipyl-CoA and CoA from succinyl-CoA and acetyl-CoA allowed efficient production of α-hydromuconic acid.

TABLE 12

| Test microorganism | Production of α-hydromuconic acid (mg/L) | | |
|---|---|---|---|
| | pBBR1MCS-2 | pBBR1MCS-2::SppcaF | pBBR1MCS-2::CgpcaF |
| Serratia grimesii NBRC13537 | 2.4 | 37.6 | 59.4 |
| Serratia ficaria NBRC102596 | 3.0 | 34.9 | 27.7 |
| Serratia fonticola NBRC102597 | 2.8 | 13.1 | 35.2 |
| Serratia odorifera NBRC102598 | 1.9 | 16.8 | 25.6 |
| Serratia plymuthica NBRC102599 | 2.5 | 8.9 | 22.5 |
| Serratia entomophila DSM12358 | 1.3 | 29.5 | 34.7 |
| Serratia nematodiphila DSM21420 | 1.4 | 16.4 | 19.8 |

(Example 15) Confirmation of the Enzymatic Activity of PcaF from S. Plymuthica NBRC102599

PcaF, which is encoded by the gene sequence represented by SEQ ID NO: 4 and cloned in Example 10, was confirmed to have the catalytic activity for the reaction to produce 3-oxoadipyl-CoA and CoA from succinyl-CoA and acetyl-CoA.

(a) Overexpression and Purification of PcaF from S. Plymuthica

The plasmid pRSF-1b was cleaved with SacI to obtain pRSF-1b/SacI. Primers (SEQ ID NOs: 11 and 12) were designed to amplify the ORF (SEQ ID NO: 4) of the pcaF gene by PCR using the genome of S. plymuthica NBRC102599 as a template, and PCR was performed conventionally. The resulting fragment and pRSF-1b/SacI were ligated together using the In-Fusion HD Cloning Kit and the resulting plasmid that was confirmed by a conventional method to have the corresponding base sequence was designated as pRSF-1b:SppcaF. Then, pRSF-1b:SppcaF was introduced into Escherichia coli BL21 (DE3) and the resulting transformant was cultured aerobically in LB medium containing 25 μg/mL kanamycin (37° C.), to which isopropylthiogalactoside was added to a final concentration of 1 mM when the OD600 reached around 0.3, to induce the expression of pcaF (aerobically, 37° C., overnight). Centrifuged bacterial cells were suspended in 20 mM Tris-HCl (pH 8.0) and disrupted on ice with an ultrasonic homogenizer and then centrifuged to recover the supernatant as a cell-free extract. The obtained cell-free extract was purified with the His-Bind Resin (manufactured by Merck) and then centrifuged in Amicon Ultra 3K (manufactured by Merck) to obtain a concentrated solution, which was then diluted with 20 mM Tris-HCl (pH 8.0) to obtain a PcaF enzyme solution (0.52 mg/mL). The concentration of the enzyme was determined using the Quick Start Bradford protein assay (manufactured by Bio-Rad Laboratories, Inc.).

(b) Measurement of the Activity of an Enzyme that Catalyzes the Reaction to Produce 3-Oxoadipyl-CoA and CoA from Succinyl-CoA and Acetyl-CoA The PcaF enzyme solution was used as an enzyme solution to measure the enzymatic activity by the same procedure as in Example 13. The result of the measurement indicated that the specific activity was 0.170 Unit/mg and the purified enzyme had the catalytic activity for the reaction to produce 3-oxoadipyl-CoA and CoA from succinyl-CoA and acetyl-CoA.

INDUSTRIAL APPLICABILITY

According to the present invention, a microorganism belonging to the genus Serratia can be used to produce α-hydromuconic acid. The obtained α-hydromuconic acid can be used as a raw material for various types of polymers.

The invention claimed is:

1. A *Serratia* microorganism capable of producing α-hydromuconic acid, wherein said microorganism comprises a gene encoding a *Serratia* or *Corynebacterium* 3-oxoadipyl-CoA thiolase (EC 2.3.174) or a gene encoding a *Serratia* or *Corynebacterium* acetyl-CoA acetyltransferase (EC 2.3.1.9), and wherein said 3-oxoadipyl-CoA thiolase or acetyl-CoA acetyltransferase is overexpressed in said microorganism, and wherein said 3-oxoadipyl-CoA thiolase or acetyl-CoA acetyltransferase activity to produce 3-oxoadipyl-CoA and CoA from succinyl-CoA and acetyl-CoA is increased in said *Serratia* microorganism compared to a control of a *Serratia* microorganism without introducing said gene.

2. The *Serratia* microorganism of claim 1, wherein said *Serratia* microorganism is *Serratia grimesii*, *Serratia ficaria*, *Serratia fonticola*, *Serratia odorifera*, *Serratia plymuthica*, *Serratia entomophila*, or *Serratia nematodiphila*.

3. A method of producing α-hydromuconic acid, said method comprising culturing the *Serratia* microorganism of claim 1, thereby producing α-hydromuconic acid.

4. The method of claim 3, wherein said *Serratia* microorganism is *Serratia grimesii*, *Serratia ficaria*, *Serratia fonticola*, *Serratia odorifera*, *Serratia plymuthica*, *Serratia entomophila*, or *Serratia nematodiphila*.

5. The method of claim 3, wherein a culture medium for culturing said *Serratia* microorganism comprises at least one or more carbon sources selected from the group consisting of saccharides, succinic acid, 2-oxoglutaric acid, and glycerol.

6. The method of claim 3, wherein said *Serratia* microorganism is cultured in a medium that comprises at least one or more inducers selected from the group consisting of ferulic acid, p-coumaric acid, benzoic acid, cis,cis-muconic acid, protocatechuic acid, and catechol.

7. The method of claim 4, wherein a culture medium for culturing said *Serratia* microorganism comprises at least one or more carbon sources selected from the group consisting of saccharides, succinic acid, 2-oxoglutaric acid, and glycerol.

8. The method of claim 4, wherein said *Serratia* microorganism is cultured in a medium that comprises at least one or more inducers selected from the group consisting of ferulic acid, p-coumaric acid, benzoic acid, cis,cis-muconic acid, protocatechuic acid, and catechol.

9. The method of claim 5, wherein said *Serratia* microorganism is cultured in a medium that comprises at least one or more inducers selected from the group consisting of ferulic acid, p-coumaric acid, benzoic acid, cis,cis-muconic acid, protocatechuic acid, and catechol.

* * * * *

SEQUENCE LISTING

```
<160> NUMBER OF SEQ ID NOS: 12

<210> SEQ ID NO 1
<211> LENGTH: 200
<212> TYPE: DNA
<213> ORGANISM: Escherichia coli
<220> FEATURE:
<221> NAME/KEY: 5'UTR
<222> LOCATION: (1)..(200)

<400> SEQUENCE: 1
cgtaattgcc ctttaaaatt cggggcgccg acccatgtg gtctcaagcc caaaggaaga      60
gtgaggcgag tcagtcgcgt aatgcttagg cacaggattg atttgtcgca atgattgaca     120
cgattccgct tgacgctgcg taaggttttt gtaattttac aggcaacctt ttattcacta     180
acaaatagct ggtggaatat                                                 200

<210> SEQ ID NO 2
<211> LENGTH: 30
<212> TYPE: DNA
<213> ORGANISM: Artificial Sequence
<220> FEATURE:
<223> OTHER INFORMATION: Artificial Sequence
```

```
<220> FEATURE:
<221> NAME/KEY: primer
<222> LOCATION: (1)..(30)

<400> SEQUENCE: 2
taccgtcgac ctcgacgtaa ttgcccttta                               30

<210> SEQ ID NO 3
<211> LENGTH: 41
<212> TYPE: DNA
<213> ORGANISM: Artificial Sequence
<220> FEATURE:
<223> OTHER INFORMATION: Artificial Sequence
<220> FEATURE:
<221> NAME/KEY: primer
<222> LOCATION: (1)..(41)

<400> SEQUENCE: 3
ggccccccct cgagtcatta agtactatat tccaccagct a                  41

<210> SEQ ID NO 4
<211> LENGTH: 1203
<212> TYPE: DNA
<213> ORGANISM: Serratia plymuthica
<220> FEATURE:
<221> NAME/KEY: gene
<222> LOCATION: (1)..(1203)

<400> SEQUENCE: 4
atgaatccag cctatctgtg tgacgccgtt cgtacgccct ttggccgtct gaacggcagt    60
ctcgccactg tccgcgccga cgatctggcc gccctgccgc tgaaagcgct acaggcgcgc   120
cacccgcagc ttgactggag cgcggtagac gacgtgttgc tcggctgcgc caaccaggcg   180
ggagaagata accgcaacgt agcacgcatg gcgctgctgc tggccggcct gccggtgcag   240
atccccggtt gcaccctcaa tcgtctgtgc ggctccagcc tggatgctgt ggcgatggcg   300
gcccgcgcca tcaagacagg tgaaagtgag ctgatgattg ccggtggcgt ggaaagcatg   360
tcgcgggcgc cgtttgtgat gggcaaagcg gagagcgcct ttagccgggc gatgaaaata   420
gaagacacca ccatgggctg gcggtttatc aatccgcaaa tgcaggcgca atacggcgtg   480
gactctatgc cgcagaccgc tgaaaacgta gccctgaagt ttggcattag ccgccaggat   540
caggatgctt cgccctgcg cagccagcaa cgcaccgcag cggcccagga aagcggtttc   600
tttgccgagc aactgatcga agtcagtctg gcgcagaaaa aaggcgaccc actgctgttc   660
cgccaggatg aacatccgcg cgccactacg ctcgaggcac tggcgaagtt gaaaccggta   720
gttaatccgc aaggtaccgt caccgccggt aatgcctccg gctgaacga cggtgcctgc   780 gcactgttgc tggccggaga gcgcggagta acccgccacg gcttggagcc aatggcgcgc   840
attgtcgcca gcgccgtgac cggcattgaa ccttcgatta tgggctttgc gccgacagag   900
gcggtgcgca aagtgctgaa aatcgccggt ctgacgctcg atcaaatgga cgttatcgaa   960
cttaacgaag ccttttgcagc gcaggcgctg gcggtgactc gtgagctggg actgagtgac  1020
gacgccgcac aggtgaaccc aaacggcggc gcgattgcgc tgggccatcc gctgggtgct  1080
tccggtggca ggctggtgat gaacgccgcc tggcaattgc agaaaacacg gggacgctac  1140
gggttatgca ccatgtgcat cggcgttggc caaggtattg cgctgatcat cgagcgggta  1200
tga                                                               1203
```

```
<210> SEQ ID NO 5
<211> LENGTH: 30
<212> TYPE: DNA
<213> ORGANISM: Artificial Sequence
<220> FEATURE:
<223> OTHER INFORMATION: Artificial Sequence
<220> FEATURE:
<221> NAME/KEY: primer
<222> LOCATION: (1)..(30)

<400> SEQUENCE: 5
ctggtggaat atagtatgaa tccagcctat                                        30

<210> SEQ ID NO 6
<211> LENGTH: 30
<212> TYPE: DNA
<213> ORGANISM: Artificial Sequence
<220> FEATURE:
<223> OTHER INFORMATION: Artificial Sequence
<220> FEATURE:
<221> NAME/KEY: primer
<222> LOCATION: (1)..(30)

<400> SEQUENCE: 6
ctcgagtcat taagttcata cccgctcgat                                        30

<210> SEQ ID NO 7
<211> LENGTH: 53
<212> TYPE: DNA
<213> ORGANISM: Artificial Sequence
<220> FEATURE:
<223> OTHER INFORMATION: Artificial Sequence
<220> FEATURE:
<221> NAME/KEY: primer
<222> LOCATION: (1)..(53)

<400> SEQUENCE: 7
ctggtggaat atagtactta gctggtggaa tatatgaacc ctcaagatat tgt              53

<210> SEQ ID NO 8
<211> LENGTH: 41
<212> TYPE: DNA
<213> ORGANISM: Artificial Sequence
<220> FEATURE:
<223> OTHER INFORMATION: Artificial Sequence
<220> FEATURE:
<221> NAME/KEY: primer
<222> LOCATION: (1)..(41)

<400> SEQUENCE: 8
ctcgagtcat taagtgttaa cttagttctc cttttcaaag a                           41

<210> SEQ ID NO 9
<211> LENGTH: 30
<212> TYPE: DNA
<213> ORGANISM: Artificial Sequence
<220> FEATURE:
<223> OTHER INFORMATION: Artificial Sequence
<220> FEATURE:
<221> NAME/KEY: primer
<222> LOCATION: (1)..(30)

<400> SEQUENCE: 9
caagagtccg gatccatgat gataaatgtg                                        30

<210> SEQ ID NO 10
<211> LENGTH: 34
<212> TYPE: DNA
<213> ORGANISM: Artificial Sequence
```

```
<220> FEATURE:
<223> OTHER INFORMATION: Artificial Sequence
<220> FEATURE:
<221> NAME/KEY: primer
<222> LOCATION: (1)..(34)

<400> SEQUENCE: 10
cgagctccca attgggatca gatctttatg actc                              34

<210> SEQ ID NO 11
<211> LENGTH: 35
<212> TYPE: DNA
<213> ORGANISM: Artificial Sequence
<220> FEATURE:
<223> OTHER INFORMATION: Artificial Sequence
<220> FEATURE:
<221> NAME/KEY: Primer
<222> LOCATION: (1)..(35)

<400> SEQUENCE: 11
cggatcccaa ttgggagctc atgaatccag cctat                             35

<210> SEQ ID NO 12
<211> LENGTH: 35
<212> TYPE: DNA
<213> ORGANISM: Artificial Sequence
<220> FEATURE:
<223> OTHER INFORMATION: Artificial Sequence
<220> FEATURE:
<221> NAME/KEY: Primer
<222> LOCATION: (1)..(35)

<400> SEQUENCE: 12
gcgccgtgta cacgagatct tcatacccgc tcgat                             35
```